US006585643B2

(12) United States Patent
Clem et al.

(10) Patent No.: US 6,585,643 B2
(45) Date of Patent: Jul. 1, 2003

(54) HEART POSITIONING DEVICE AND METHODS

(75) Inventors: Michael F. Clem, Maineville, OH (US); Christopher J. Hess, Lebanon, OH (US); Gary W. Knight, West Chester, OH (US); Kristin L. Jambor, Cincinnati, OH (US); Ronald J. Kolata, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 8 days.

(21) Appl. No.: 09/815,065

(22) Filed: Mar. 22, 2001

(65) Prior Publication Data

US 2002/0137989 A1 Sep. 26, 2002

(51) Int. Cl.[7] .................................................. A61B 1/32
(52) U.S. Cl. ......................... 600/210; 600/217; 600/37
(58) Field of Search ................................. 600/201, 206, 600/209, 210, 217, 37; 606/144

(56) References Cited

U.S. PATENT DOCUMENTS

| | | | |
|---|---|---|---|
| 3,951,138 A | 4/1976 | Akopov | 128/17 |
| 5,415,160 A | 5/1995 | Ortiz et al. | 128/20 |
| 5,507,796 A | 4/1996 | Hasson | 606/148 |
| 5,540,648 A | 7/1996 | Yoon | 600/114 |
| 5,577,993 A * | 11/1996 | Zhu et al. | 600/210 |
| 5,702,352 A | 12/1997 | Kimura et al. | 600/201 |
| 5,713,910 A | 2/1998 | Gordon et al. | 606/144 |
| 5,954,057 A | 9/1999 | Li | 128/898 |
| 5,964,699 A * | 10/1999 | Rullo et al. | 600/217 |
| 6,015,382 A | 1/2000 | Zwart et al. | 600/207 |
| 6,126,665 A | 10/2000 | Yoon | 606/144 |
| 6,132,370 A | 10/2000 | Furnish et al. | 600/235 |
| 6,287,250 B1 * | 9/2001 | Peng et al. | 600/218 |

* cited by examiner

Primary Examiner—Cary E. O'Connor
(74) Attorney, Agent, or Firm—Nutter McClennen & Fish LLP

(57) ABSTRACT

A medical instrument for positioning an internal organ during a surgical procedure is provided. In one embodiment, the medical instrument includes a body having a tissue grasping element and at least one suspending member. The suspending member has a first end and a second end that is attached to a portion of the body. In use, the tissue grasping element penetrates a portion of the tissue on or near the body organ. Tension can then be applied to the suspending members to reposition and secure the body organ.

61 Claims, 7 Drawing Sheets

HEART POSITIONING DEVICE AND METHODS

FIELD OF THE INVENTION

The present invention relates to methods and apparatuses for positioning a body organ, and more particularly, to medical instruments that assist in manipulating and suspending a patient's heart at a desired position during diagnostic and surgical procedures.

BACKGROUND OF THE INVENTION

Coronary artery disease results in a narrowing of the coronary arteries, which are the blood vessels that supply the heart with oxygen and nutrients. There are two main coronary arteries: the left main coronary artery, which supplies blood to the left ventricle, and the right main coronary artery, which supplies blood to the right ventricle as well as the posterior surface of the left ventricle. These main coronary arteries give rise to several branches that extend into the heart muscle (myocardium), bringing vital nutrients to each muscle cell. The heart relies on these nutrients as it works constantly to pump blood through the body. Narrowing of the coronary arteries reduces blood flow to the myocardium and, if untreated, can damage and/or destroy the heart muscle.

In some cases, coronary artery disease may be treated by the use of drugs and or by modifications in behavior and diet. For certain patients, however, a coronary artery bypass graft (CABG) procedure is the preferred form of treatment to restore adequate blood flow. A CABG procedure improves the flow of blood and ensures that the heart muscle is receiving an adequate supply of oxygen-rich blood.

In a CABG procedure, a blocked section of the artery is literally "bypassed" by attaching a healthy segment of blood vessel downstream from the diseased or blocked area. During surgery, an incision is made in the patient's chest and the sternum is divided to allow access to the pericardial sac, which envelops and protects the heart.

Some CABG procedures can be performed with a beating heart, while others require that the heart be arrested, usually by administering a chemical solution, called cardioplegia, that temporarily paralyzes the heart muscle fibers. In procedures where the heart is arrested, circulation is maintained by a heart-lung machine.

During the procedure, manual manipulation and repositioning of the heart is usually necessary to access the blocked arteries. The posterior descending artery, for example, lies on the posterior surface of the heart. The surgeon or a surgical assistant is therefore required to lift and rotate the heart to expose the artery. Often, a surgeon uses his or her own hands to position the heart. However, it is difficult to maintain the heart in a secure and proper position by such techniques. In addition, direct manual contact with the heart may impair circulation, leading to reductions in cardiac output and blood pressure. Care must be exercised to avoid trauma to the heart or pericardial sac to avoid the formation of excessive adhesions.

In order to overcome these problems, devices such as slings and balloons have been developed to help position and/or stabilize the heart. A balloon, for example, is placed underneath the heart and is thereafter inflated to lift the heart into a desired position. A sling, on the other hand, is a fabric or plastic based device that is placed around the heart in the manner of a hammock. The heart can then be positioned by moving the sling.

While attempts have been made to support the heart during a CABG surgery, the resulting devices and techniques have several drawbacks that have hindered their acceptance in the art. For example, slings made of net or fabric tend to interfere with access to the surgical target. Moreover, net slings require special techniques or procedures to remove the net from the surgical target area. Where a balloon is employed, the heart is freely slidable on the balloon, and not necessarily securely positioned, thus posing a risk of damage during the surgical procedure. Moreover, if a balloon is over-inflated, it can exert excess pressure on the heart, potentially causing damage to the heart.

In addition to the aforementioned problems, the recent trend in moving toward less invasive procedures makes placement of a sling or inflatable balloon nearly impossible. A minimally invasive direct coronary artery bypass (MIDCAB) procedure is a new technique which, compared with standard cardiac procedures, causes less pain, speeds recovery, and delivers identical results at less cost.

MIDCAB procedures are usually performed on the beating heart, thereby eliminating the expense and risk of stopping the heart and the necessity of a heart-lung bypass machine. The procedure is performed by making an incision in the chest (thorocotomy). A heart stabilizer can be used to restrict movement of the heart within the limited surgical field.

Since the surgeon is operating on a beating heart, both movement and blood can cause a sling or balloon to displace during surgery. Moreover, the surgeon's ability to access and manipulate the heart is hampered since the incision used to access the thoracic cavity is much smaller. As a result, the limited surgical field makes placement of any type of inflatable balloon or sling around the heart very difficult.

Surgeons have also employed retraction sutures and retraction tapes to lift and secure the heart during surgical procedures. In this technique a number of retraction sutures (e.g., three) are placed deep within the pericardium and then tensioned to lift the heart. In another technique, retraction tapes, which are usually thick, porous straps, are placed strategically around the heart. The tapes are then gradually retracted to reposition the heart and expose the target artery. Typically, two pairs of retraction tapes are employed. The first pair is passed through the transverse sinus, and the second pair is passed beneath the inferior vena cava. One end of each tape is fixed to a stationary support and the other end of each tape is kept free. The free ends can then be retracted to position the heart. Once the heart is in the desired position, the free ends of the tapes can be secured to the support.

The use of retraction sutures and retraction tapes has some drawbacks in that it is difficult and time consuming to place these devices properly while avoiding risk of damage to the heart.

For example, when sutures are used, the tip of the suture needle must be placed along the pericardium, and then rotated to penetrate through the tissue. Unpredictable motion of the epicardial surface during needle placement may cause laceration of the heart or puncture of a coronary artery. A high degree of skill is also required to grasp the proper amount of tissue. If an insufficient amount of tissue is engaged, the suture may tear through the tissue and fail. Conversely, if too much tissue is engaged, the suture may penetrate and possibly damage an underlying organ, such as the lung.

The proper placement of retraction tapes is made difficult due to the limited surgical field and reduced field of vision.

Moreover, the procedure can be time consuming and risky since a pair of retraction tapes needs to be placed through the transverse sinus. Traumatic stressing of the transverse sinus, or excessive destruction of the tissue, can lead to stenosis, further compromising the patient's health. Further, the placement of retraction tapes directly around the heart can lead to a significant drop in blood pressure.

Accordingly, there is a need for an organ positioning and manipulating device which can be easily, quickly, and safely employed to present and expose target surgical tissue.

SUMMARY OF THE INVENTION

The present invention provides a medical instrument for positioning an internal organ during a surgical procedure. In one embodiment, the medical instrument includes a body having a tissue grasping element and at least one suspending member. The suspending member has a first free end and a second end attached to a portion of the body. In use, the tissue grasping element penetrates a portion of the tissue on or near the body organ. Tension can then be applied to the suspending members to reposition and secure the body organ.

In certain aspects of the invention, the tissue grasping element has a tissue piercing end and a connection end. The connection end of the tissue grasping element is pivotably attached to the body and movable between a closed position and an open position. The tissue grasping element may be biased to a closed position. An actuating member formed within the body is effective to move the tissue grasping element selectively between the open position and the closed position. In another embodiment, the body is substantially disk-shaped, and can include one surface that is concave. The body can also include several tissue engaging teeth present on a side surface of the body adjacent to the tissue grasping element.

In another embodiment, the body includes a first portion oriented in a first plane, and a second portion oriented in a second plane. The second plane is substantially orthogonal to the first plane. The second portion can be flexible and movable from a position coplanar with the first portion to a position orthogonal to the first portion. In further aspects, the body includes a mating element for selectively mating with a positioning tool.

The invention also encompasses a medical system effective to assist in positioning an internal organ during a surgical procedure. The medical system includes a body having a tissue grasping element and at least one suspending member having a first end and a second end. A positioning tool, matable with a portion of the body, is provided to manipulate and properly place the body. The positioning tool can include a sheath defining an inner lumen that receives at least a portion of the at least one suspending member. In one embodiment, the positioning member is also used to actuate a mechanism that selectively deploys the tissue grasping element.

The present invention also provides a method for positioning a body organ. The method involves providing a medical instrument having a body, a tissue grasping element appended to the body, and at least one suspending member having a first end and a second end, the second end attached to a portion of the body; positioning the body in proximity to an internal organ to be repositioned; manipulating the body so that the tissue grasping element grasps a desired portion of tissue; and applying tension to the at least one suspending member to reposition and secure the body organ. The medical instrument can also include a mating element effective to enable the instrument to selectively mate with a positioning tool to facilitate positioning of the body.

BRIEF DESCRIPTION OF THE DRAWINGS

The invention will be more fully understood from the following detailed description taken in conjunction with the accompanying drawings, in which like reference numerals designate like parts throughout the figures, and wherein.

DETAILED DESCRIPTION OF THE INVENTION

Figure 1:
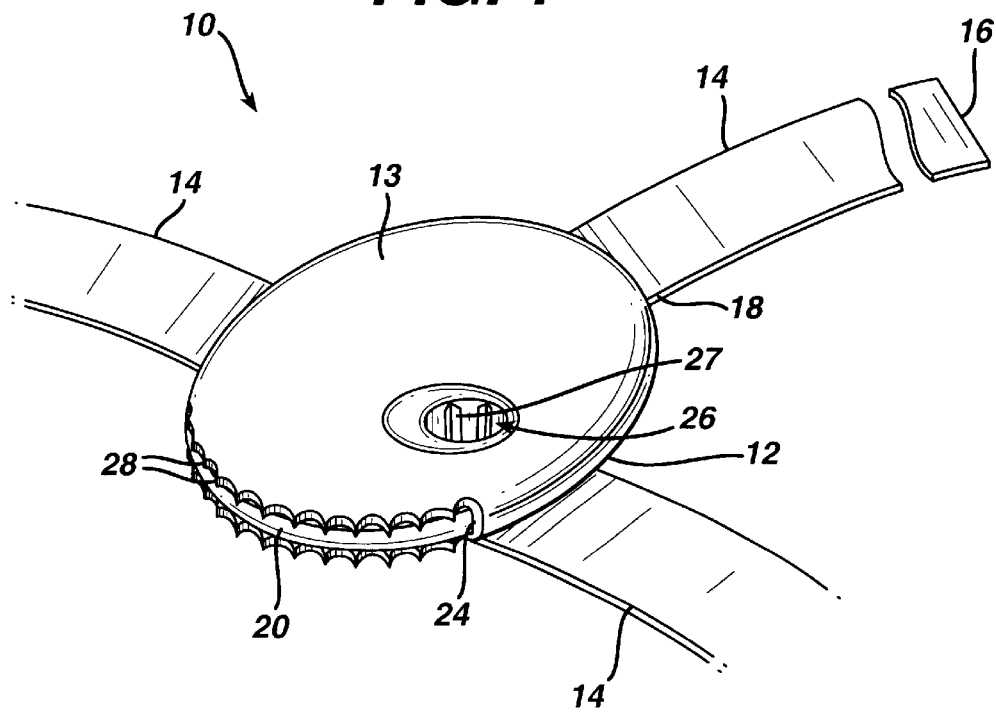
FIG. 1 is a perspective view of a medical instrument according to one embodiment of the present invention.

The present invention relates to a medical instrument for assisting in manipulating and suspending a body organ at a desired position during diagnostic and surgical procedures. The medical instrument of the present invention is particularly useful for positioning a patient's heart during a coronary artery bypass procedure. The instrument can be easily, quickly, and safely employed to present and expose target surgical tissue.

In general, the medical instrument according to the present invention includes a body 12, 32 having a tissue grasping element 20, 40 and at least one suspending member 14, as shown in FIGS. 1–5. Each suspending member 14 has a first, free end 16, and a second end 18 mated to the body 12, 32. The tissue grasping element 20, 40 penetrates a portion of the tissue on or near the body organ. The free ends 16 can then be retracted to position the heart. Once the heart is in the desired position, the free ends 16 of the suspending members 14 can be secured to a support.

The body 12, 32 of the medical instrument 10 can be formed from a rigid or semi-rigid material. Suitable materials include plastic, light weight metal or metal alloy, or a composite material. Preferably, the body 12, 32 is made of a biocompatible material, such as, for example, titanium or a titanium alloy, or a variety of rigid polymers known to be useful in medical devices. The size of the body is preferably between about 0.5" and 1.5" in diameter, and more preferably about 1" in diameter. While FIGS. 1–5 illustrate a substantially disk-shaped body, the body 12, 32 can have any shape and form, such as rectangular, square, oval, and other such shapes. It is understood that any square or rectangular shaped bodies should have substantially rounded corners and/or edges.

The tissue grasping element 20, 40 can also be made from a rigid or semi-rigid material, such as plastic, light weight metal or metal alloy, or a composite material. Preferably, the tissue grasping element is made from stainless steel. The tissue grasping element 20, 40 can be removably appended to the body to optionally allow the tissue grasping element to be replaced after use. Alternatively, the tissue grasping element 20, 30 can be integral with the body 12, 32. The tissue grasping element 20, 20 can be disposed at any location on the body 12, 32, but is preferably disposed along the outer edge of the body 12, 32. In one embodiment, the tissue grasping element 20, 40 of the present invention is a tissue penetrating member, such as a needle. Any standard size needle can be used. However, the tissue grasping element is preferably an SH½ circular needle, a CT2 needle, or a V-7 needle.

The suspending members 14 of the present invention can be made from any material that is substantially inelastic and/or flexible. Suitable materials and structures from which the suspending members 14 can be made include straps, cords, sutures, and bands. Alternatively, the suspending members 14 can be made from an elastic material, such as latex or silicone. The second end 18 of each suspending member 14 is attached to the body. A rivet, screw, snap, buckle, adhesive, or similar attachment device can be used secure the second end 18 of each suspending member 14 to the body 12, 32. The length of each suspending member 14 should be sufficient to allow the first end 16 of the suspending members 14 to be tied to a support element.

FIG. 1 illustrates one embodiment of a medical instrument 10 having a body 12, three suspending members 14, and a tissue grasping element 20. The body 12 can be substantially disk-shaped and can include a first surface 13 that is concave, an opposed second surface, and a peripheral side surface. Each suspending member includes a first end 16 and a second end 18. The second end 18 is mated to the body 12. The tissue grasping element 20 has a tissue piercing end 22 (shown in FIG. 4) and a connection end 24. The body 12 can also include several tissue engaging teeth 28 present at least on a portion of a side surface of the body adjacent to the tissue grasping element 20.

Figure 2:
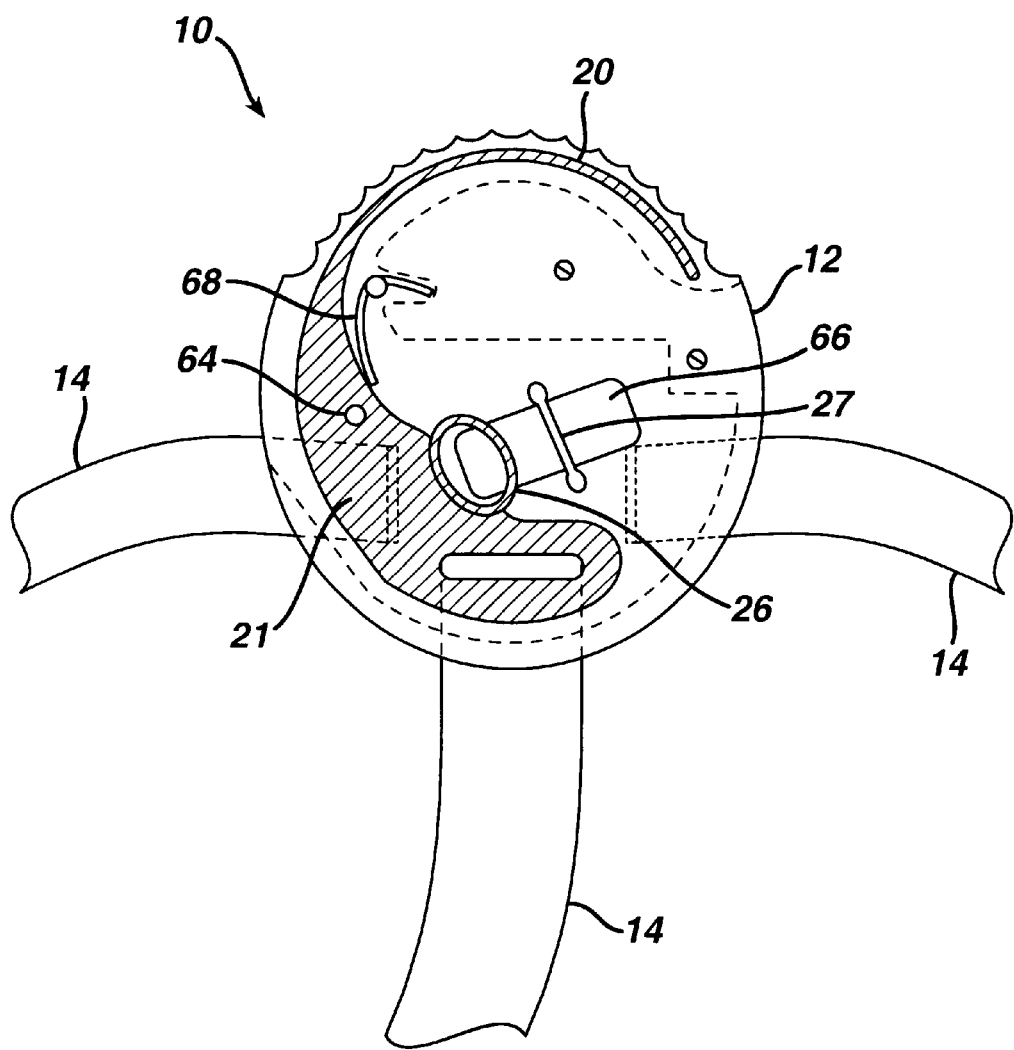
FIG. 2 is a top view, partially cut away, of the medical instrument of FIG. 1.
Figure 3:
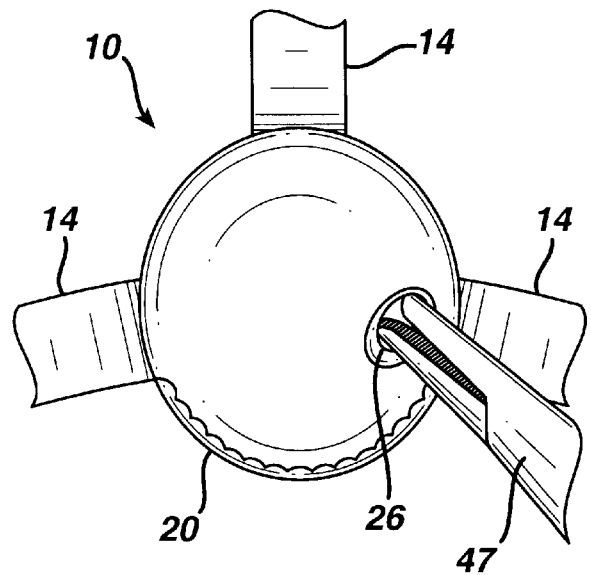
FIG. 3 is a perspective view of the medical instrument of FIG. 1 in a closed position and including a positioning tool according to the present invention.
Figure 4:
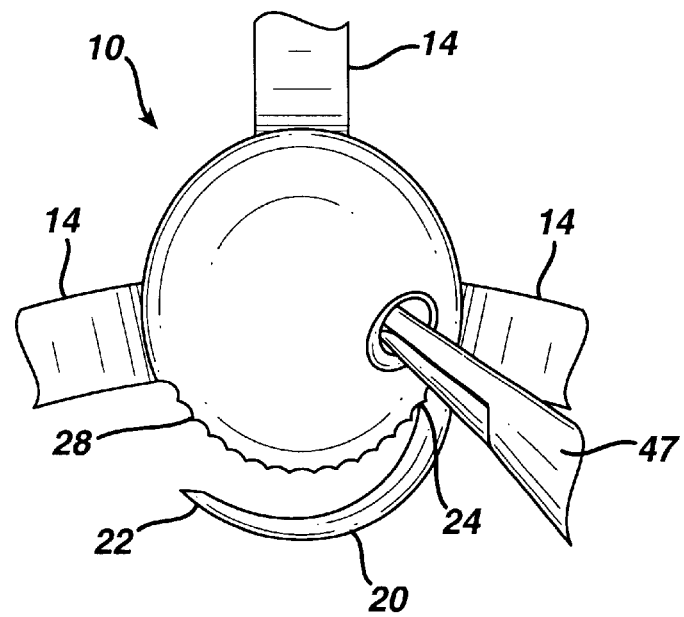
FIG. 4 is a perspective view of the medical instrument of FIG. 1 in an open position, actuated by the positioning tool of FIG. 3.

As shown in FIGS. 1–4, the tissue grasping element 20 is pivotably attached to the body at the connection end 24, and is movable between an open position (shown in FIG. 4) and a closed position (shown in FIGS. 1 through 3). The tissue grasping element is preferably biased to the closed position.

An actuating member 26 formed within the body 12 can be provided for moving the tissue grasping element 20 between the open and closed positions. The connection end 24 of the tissue grasping element 20 can extend into the body 12 to mate, directly or indirectly, with the actuating member 26. A rigid element 27, such as a stationary brace, can be disposed adjacent the actuating member 26 for grasping and moving the actuating member 26 with respect to the body 12.

As shown in FIG. 2, the tissue grasping element 20 is distally appended to a rotatable body 21 that is rotatably disposed within body 12. Preferably, rotatable body 21 is secured by and rotatable about pivot point 64. FIG. 2 further illustrates that a spring 68 biases the tissue engaging element 20 to the closed position. The biasing force can be overcome by causing the rotatable body to rotate about pivot point 64, thus pulling tissue grasping element 20 away from body 12. In an exemplary embodiment, the top surface of body 12 includes an opening 66 that exposes an actuating member 26 appended to rotatable body 21. An instrument may be used to apply a force to the actuating member 26 and rotatable body 21 sufficient to overcome the biasing force.

FIG. 2 illustrates an embodiment in which a stationary brace 27 bridges opening 66. A separate element, such as a positioning tool 47 shown in FIGS. 3 and 4, can be used to pinch actuating member 26 towards stationary brace 27. Upon release of the actuating member the spring 68 causes the tissue grasping element 20 to return to the closed position.

Figure 5:
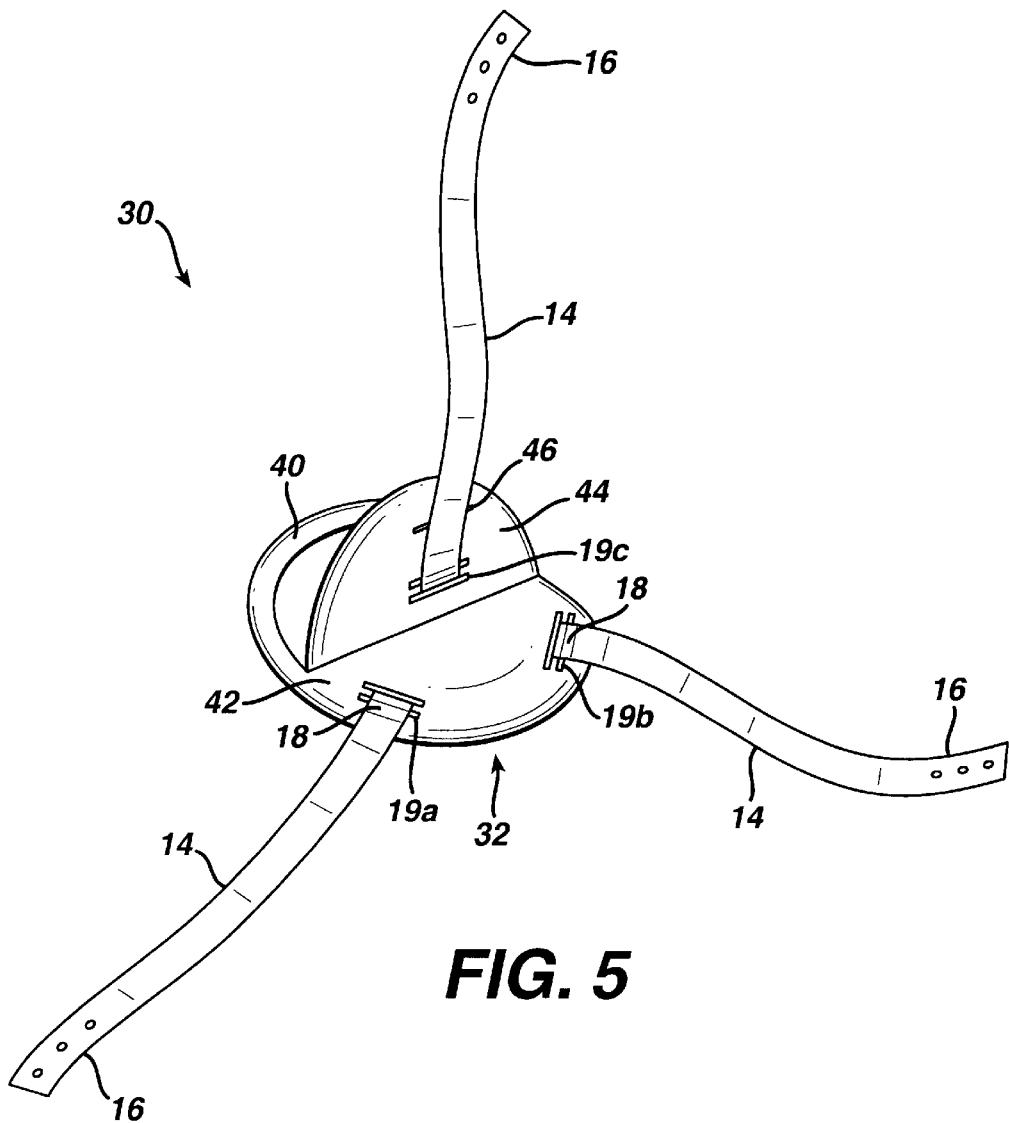
FIG. 5 is a perspective view of a medical instrument according to another embodiment of the present invention.

FIG. 5 illustrates another embodiment of a medical system 30 having a body 32, a tissue grasping element 40, and three suspending members 14. In one embodiment, the body 32 has a first portion 42 that is oriented in a first plane, and a second portion 44 that is oriented in a second plane that is substantially orthogonal to the first plane. In another embodiment, the second portion 44 is flexible and can be oriented in several different planes with respect to the first portion 42. Accordingly, the second portion 44 can be movable from a position coplanar with the first portion 42 to a position orthogonal to the first portion 42. The tissue grasping element 40 is preferably coplanar with the first portion 42 of the body 32.

The suspending members 14 can be disposed anywhere on the body 12. By way of non-limiting example, the second end 18 of each suspending member 14 can each be looped through a slot on the body 32 and then sewn or adhered to itself to secure the suspending member 14 to the body. Two slots 19a, 19b can be formed in the first portion of the body, and a third slot 19c can be formed in the second portion of the body 32. While FIGS. 5 and 6 illustrates slots 19a–c for securing the suspending members 14 to the body 32, any type of adhesive, buckle, snap, rivet, or similar attachment device can be used.

Figure 6:
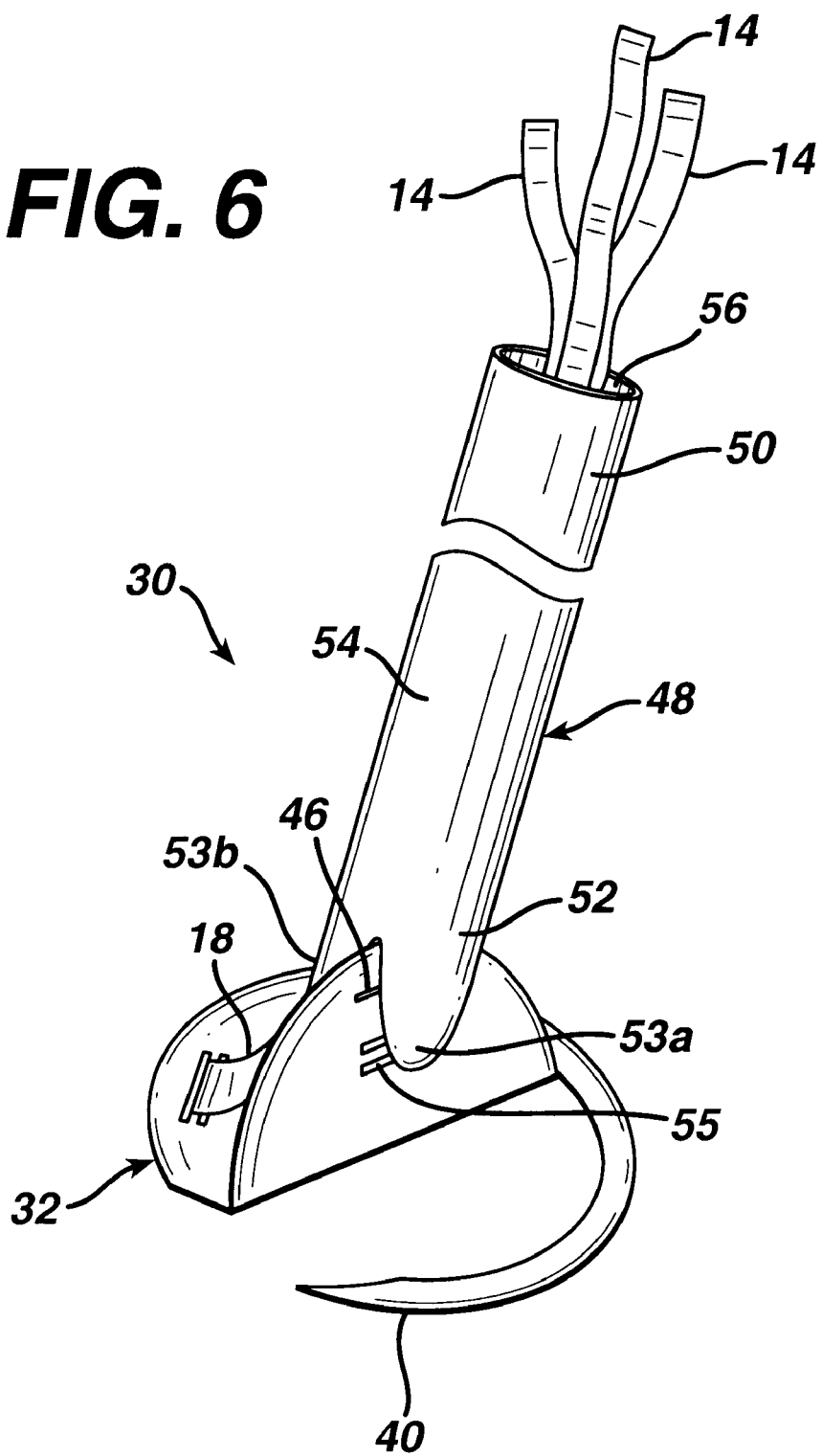
FIG. 6 is a perspective view of the medical instrument of FIG. 5 together with a positioning tool.

As shown in FIGS. 5 and 6, the body 32 can include a mating element 46 effective to enable the instrument 10 to selectively mate with a positioning tool 48. In an exemplary embodiment the mating element 46 is an upper, protruding portion of the second portion 44 of the body 32. Alternatively, the mating element 46 can be, for example, a cut out portion in the second portion 44 of the body 32 for receiving a clamp or other type of grasping member disposed on the positioning tool 48.

The positioning tool 48 includes a proximal end 50 and a distal end 52. The distal end 52 is selectively matable with the mating element 46 of the body 32. In one embodiment, the distal end is substantially of a "duck-bill" shape, having a slit 55 separating two elements 53a, 53b of the distal end 52. The slit 55 is dimensioned and adapted to engage mating element 46 between elements 53a, 53b. The positioning tool 48 further includes a sheath 54 that defines an inner lumen 56. The inner lumen 56 is adapted to receive at least a portion of the suspending members 14, as shown in FIG. 6.

The positioning tool 48 can be made from a variety of materials, including those that are malleable. Suitable materials and structures from which the positioning tool 48 can be made include plastic, metal or metal alloys, and composite materials.

In use, the positioning tool 48 is effective to manipulate the body when mated thereto. In one embodiment, the suspending members 14 are pulled through the inner lumen 56 of the sheath 54 and held with tension to secure the positioning tool 48 onto the mating element 46. The positioning tool 48 is then used to manipulate the body and cause the tissue grasping element 40 to penetrate tissue. The suspending members 14 can then be released and the positioning tool 48 slid off of the body 32.

In another embodiment, the positioning tool 48 includes a grasping member or clamp (not shown) disposed on the distal end of the positioning tool 48 for grasping the mating element 46. A controlled release mechanism can be provided on the positioning tool 48 for releasing the mating element 46. In yet another embodiment, a loose interference fit can be used to mate the positioning tool 48 and the mating element 46.

The medical instrument of the present invention can be used for positioning any body organ, but is preferably used for positioning a patient's heart. The procedure involves positioning the body in proximity to the internal organ to be repositioned, and then manipulating the body so that the tissue grasping element penetrates a desired portion of tissue. Tension can then be applied to the suspending members to reposition and secure the body organ. Once the organ is properly positioned, the free end of the suspending members can be secured to a support.

Figure 7:
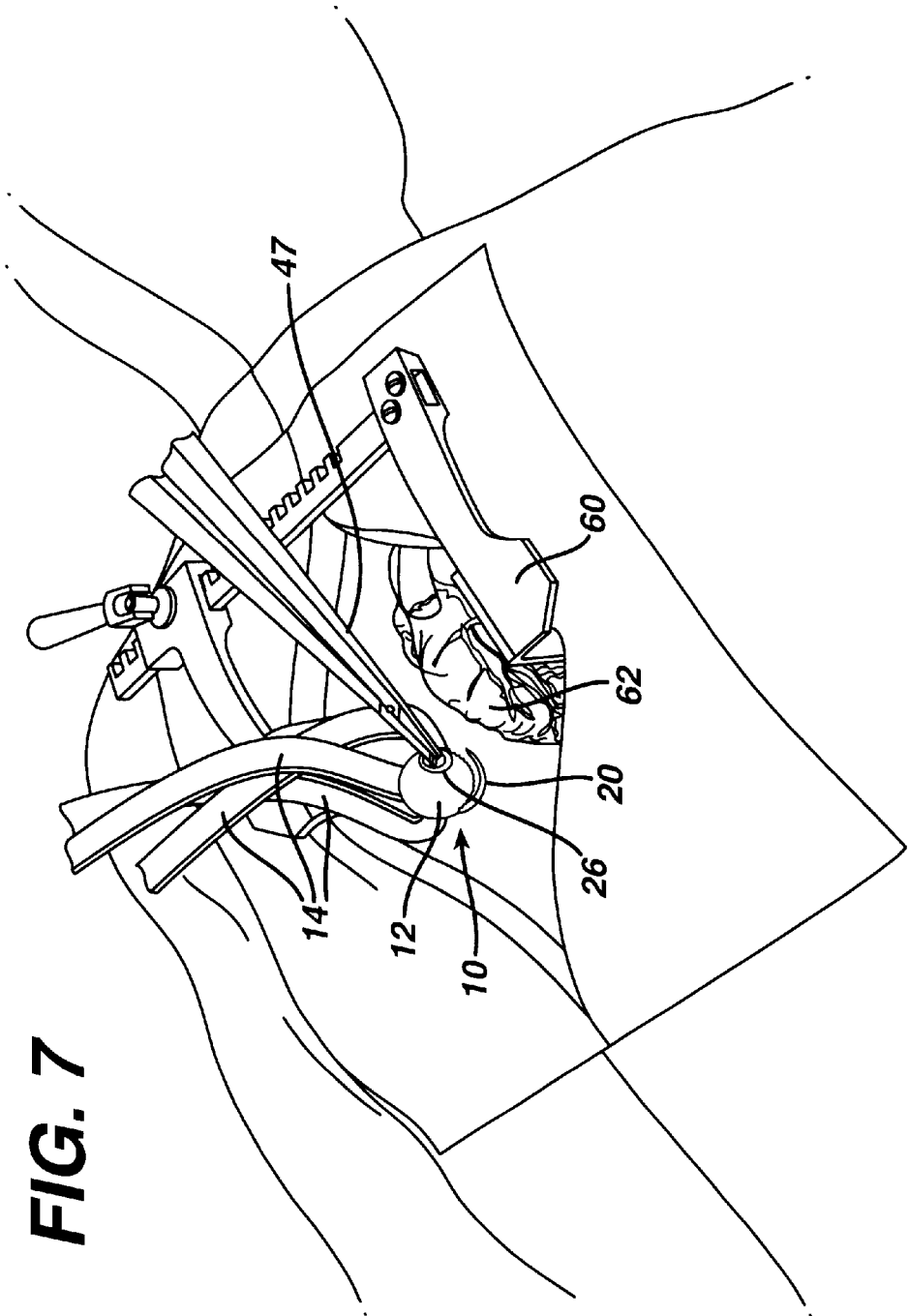
FIG. 7 is a diagram of a medical instrument and system of the present invention in use during a surgical procedure before engaging tissue.
Figure 8:
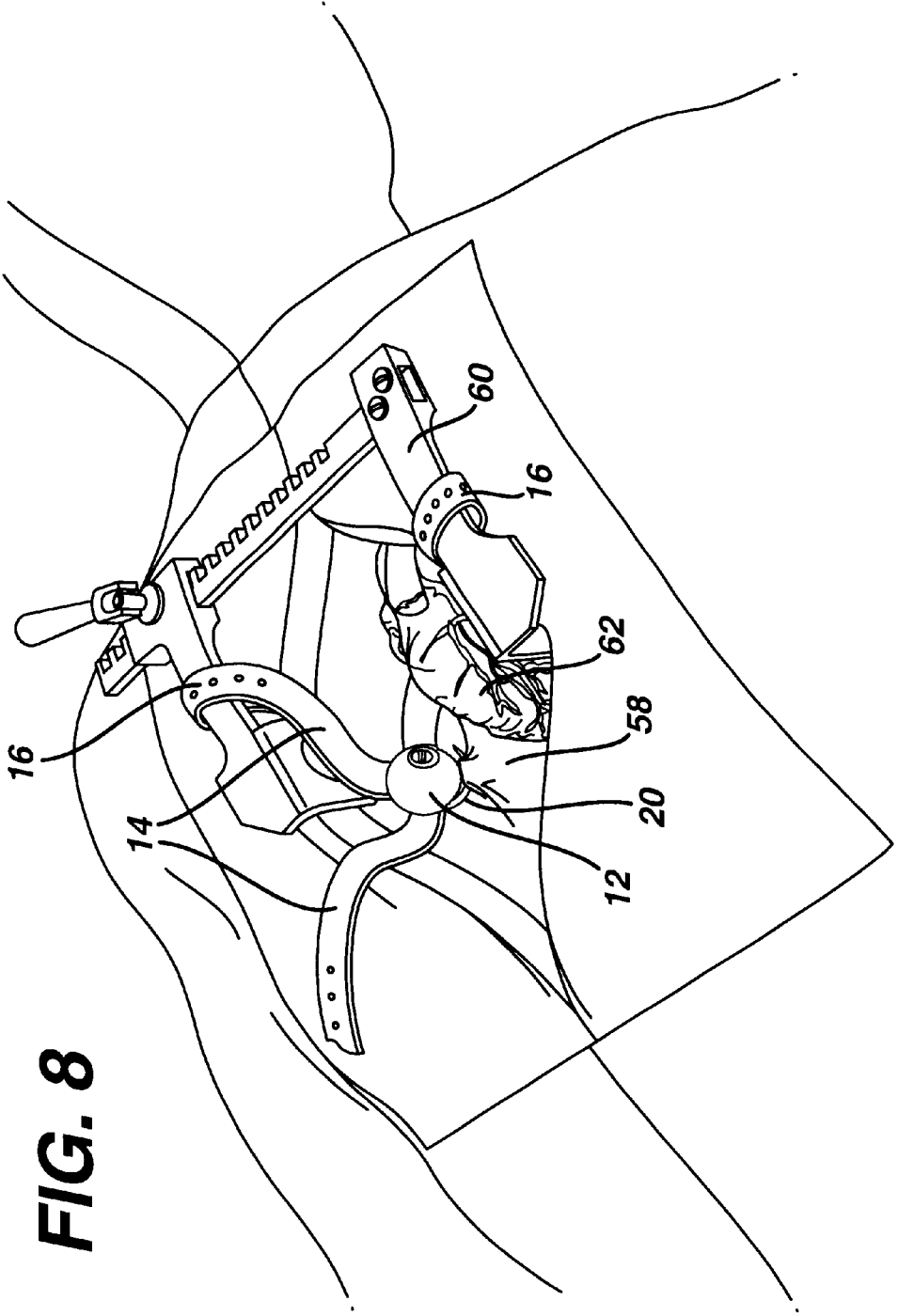
FIG. 8 is another illustrative diagram of the medical instrument and system of FIG. 6 in use during a surgical procedure after engaging tissue.

By way of non-limiting example, FIGS. 7 and 8 illustrate a medical instrument 10 used for positioning a patient's heart 62. The medical instrument has a body 12, a tissue grasping element 20, and an actuating member 26 formed within the body 12 effective to move the tissue grasping element 20 selectively between an open position and a closed position. A positioning tool 47 is provided for manipulating the medical instrument 10. In use, the actuating member 26 is grasped by the positioning tool 47, thereby moving the tissue grasping element 20 to the open position. The positioning tool 47 is then manipulated to rotate the body 10 thereby causing the tissue grasping element 20 to penetrate a desired portion of tissue, e.g., the pericardium 58, as shown in FIG. 8. The actuating member 26 is then released and the positioning tool 47 is removed. Tension can then be applied to the suspending members 14 to reposition and secure the heart 62. The first end 16 of the suspending members 14 can be secured to a support member 60, e.g., a retractor.

Those having ordinary skill in the art will know, or be able to ascertain, using no more than routine experimentation, many equivalents to the specific embodiments of the invention described herein. These and all other equivalents are intended to be encompassed by the following claims. All publications and references cited herein including those in the background section are expressly incorporated herein by reference in their entirety.

What is claimed is:

1. A medical instrument effective to assist in positioning an internal organ during a surgical procedure, comprising:
    a substantially disk-shaped body;
    a tissue grasping element appended to the body; and
    at least one suspending member having a first end and a second end, the second end being attached to a portion of the body.

2. The instrument of claim 1, wherein the body has a first surface that is concave.

3. The instrument of claim 1, wherein the body includes a first portion that is oriented in a first plane.

4. The instrument of claim 3, wherein the body includes a second portion that is oriented in a second plane.

5. The instrument of claim 4, wherein the second plane is substantially orthogonal to the first plane.

6. The instrument of claim 5, wherein the tissue grasping element is coplanar with the first portion.

7. The instrument of claim 6, wherein the tissue grasping element has a tissue piercing end and a connection end.

8. The instrument of claim 6, wherein the tissue grasping element is integral with the first portion of the body.

9. The instrument of claim 4, wherein the second portion is flexible and is able to be selectively oriented in a plurality of planes.

10. The instrument of claim 9, wherein the second portion is movable from a position coplanar with the first portion to a position orthogonal to the first portion.

11. The instrument of claim 1, wherein the tissue grasping element has a tissue piercing end and a connection end.

12. The instrument of claim 11, wherein the connection end of the tissue grasping element is pivotably attached to the body.

13. The instrument of claim 12, wherein the tissue grasping element is movable between a closed position and an open position.

14. The instrument of claim 13, wherein the tissue grasping element is biased to the closed position.

15. The instrument of claim 14, wherein an actuating member is formed within the body and is effective to move the tissue grasping element selectively between the open position and the closed position.

16. The instrument of claim 15, wherein a plurality of tissue engaging teeth are present on at least a portion of a side surface of the body adjacent to the tissue grasping element.

17. The instrument of claim 1, wherein the tissue grasping element is a tissue penetrating member.

18. The instrument of claim 17, wherein the tissue penetrating member is curvilinear.

19. The instrument of claim 18, wherein the tissue penetrating member is a needle.

20. The instrument of claim 1, wherein a mating element is formed on the body, and the mating element is effective to enable the instrument to selectively mate with a positioning tool.

21. The instrument of claim 1, wherein three suspending members are attached to the body, each at the second end thereof.

22. The instrument of claim 21, wherein the first end of each of the three suspending members is adapted to be secured to a support member.

23. The instrument of claim 1, wherein the at least one suspending member is flexible.

24. The instrument of claim 23, wherein the at least one suspending member is inelastic.

25. The instrument of claim 24, wherein the suspending member is selected from the group consisting of a strap, a band, a tape, and a string.

26. A medical system effective to assist in positioning an internal organ, during a surgical procedure, comprising
    a body having a mating element;
    a curvilinear tissue grasping element appended to the body;
    at least one suspending member having a first end and a second end, the second end being appended to a portion of the body; and
    a positioning tool selectively matable with the mating element, the positioning tool being effective to manipulate the body when mated thereto.

27. The medical system of claim 26, wherein the positioning tool has a proximal end and a distal end, the distal end being selectively matable with the mating element of the body.

28. The medical system of claim 26, wherein at least a portion of the positioning tool includes a sheath defining an inner lumen.

29. The medical system of claim 28, wherein the inner lumen is adapted to receive at least a portion of the at least one suspending member.

30. The medical system of claim 26, wherein at least a portion of the positioning tool is malleable.

31. The medical system of claim 26, wherein the tissue grasping element is selectively movable between an open position and a closed position.

32. The medical system of claim 31, wherein the tissue grasping element is biased to the closed position.

33. The medical system of claim 32, wherein the mating element comprises an actuating member that is selectively manipulatable by the positioning tool to move the tissue grasping element between the open and closed positions.

34. A method for positioning a body organ, comprising:
    providing a medical instrument having a substantially disk-shaped body, a tissue grasping element appended to the body, and at least one suspending member having a first end and a second end, the second end attached to a portion of the body;
    positioning the body in proximity to an internal organ to be repositioned;
    manipulating the body so that the tissue grasping element grasps a desired portion of tissue; and
    applying tension to the at least one suspending member to reposition and secure the body organ.

35. The method of claim 34, wherein the medical instrument includes a mating element effective to enable the instrument to selectively mate with a positioning tool to facilitate positioning of the body.

36. The method of claim 34, wherein the tissue grasping element penetrates a desired portion of tissue.

37. A medical instrument effective to assist in positioning an internal organ during a surgical procedure, comprising:
    a body having a first portion that is oriented in a first plane, and a second portion that is oriented in a second plane that is substantially orthogonal to the first plane, the second portion being flexible and able to be selectively oriented in a plurality of planes;
    a tissue grasping element appended to the body; and
    at least one suspending member having a first end and a second end, the second end being attached to a portion of the body.

38. The instrument of claim 37, wherein the second portion is movable from a position coplanar with the first portion to a position orthogonal to the first portion.

39. The instrument of claim 37, wherein the tissue grasping element is coplanar with the first portion.

40. The instrument of claim 37, the tissue grasping element is integral with the first portion of the body.

41. A medical instrument effective to assist in positioning an internal organ during a surgical procedure, comprising:
    a body;
    a tissue grasping element appended to the body and having a tissue piercing end and a connection end, the connection end being pivotally attached to the body and movable between a closed position and an open position, the tissue grasping element being biased to the closed position; and
    at least one suspending member having a first end and a second end, the second end being attached to a portion of the body.

42. The instrument of claim 41, wherein an actuating member is formed within the body and is effective to move the tissue grasping element selectively between the open position and the closed position.

43. The instrument of claim 42, wherein a plurality of tissue engaging teeth are present on at least a portion of a side surface of the body adjacent to the tissue grasping element.

44. A medical instrument effective to assist in positioning an internal organ during a surgical procedure, comprising:
    a body;
    a curvilinear tissue penetrating member appended to the body; and
    at least one suspending member having a first end and a second end, the second end being attached to a portion of the body.

45. The instrument of claim 44, wherein the tissue penetrating member is a needle.

46. The instrument of claim 44, wherein the body is substantially disk-shaped and has a first surface that is concave.

47. The instrument of claim 44, wherein a mating element is formed on the body, and the mating element is effective to enable the instrument to selectively mate with a positioning tool.

48. The instrument of claim 44, wherein three suspending members are attached to the body, each at the second end thereof.

49. The instrument of claim 48, wherein the first end of each of the three suspending members is adapted to be secured to a support member.

50. The instrument of claim 44, wherein the at least one suspending member is flexible.

51. The instrument of claim 50, wherein the at least one suspending member is inelastic.

52. The instrument of claim 51, wherein the suspending member is selected from the group consisting of a strap, a band, a tape, and a string.

53. A medical system effective to assist in positioning an internal organ, during a surgical procedure, comprising
    a body having a mating element;
    a tissue grasping element appended to the body and selectively movable between an open position and a closed position, the tissue grasping element being biased to the closed position;
    at least one suspending member having a first end and a second end, the second end being appended to a portion of the body; and
    a positioning tool selectively matable with the mating element, the positioning tool being effective to manipulate the body when mated thereto.

54. The medical system of claim 53, wherein the mating element comprises an actuating member that is selectively manipulatable by the positioning tool to move the tissue grasping element between the open and closed positions.

55. A method for positioning a body organ, comprising:
    providing a medical instrument having a body, a curvilinear tissue grasping element appended to the body, and at least one suspending member having a first end and a second end, the second end attached to a portion of the body;
    positioning the body in proximity to an internal organ to be repositioned;
    manipulating the body so that the tissue grasping element grasps a desired portion of tissue; and
    applying tension to the at least one suspending member to reposition and secure the body organ.

56. The method of claim 55, wherein the medical instrument includes a mating element effective to enable the instrument to selectively mate with a positioning tool to facilitate positioning of the body.

57. A method for positioning a body organ, comprising:
providing a medical instrument having
   a body including a first portion extending in a first plane, a second portion extending in a second plane that is substantially orthogonal to the first plane, the second portion being flexible and able to be oriented in a plurality of planes,
   a tissue grasping element appended to the body, and
   at least one suspending member having a first end and a second end, the second end attached to a portion of the body;
positioning the body in proximity to an internal organ to be repositioned;
manipulating the body so that the tissue grasping element grasps a desired portion of tissue; and
applying tension to the at least one suspending member to reposition and secure the body organ.

58. The method of claim 57, wherein the medical instrument includes a mating positioning felement effective to enable the instrument to selectively mate with a positioning tool to facilitate of the body.

59. A method for positioning a body organ, comprising:
providing a medical instrument having
   a body,
   a tissue grasping element appended to the body and movable between an open position and a closed position, the tissue grasping element being biased to the closed position, and
   at least one suspending member having a first end and a second end, the second end attached to a portion of the body;
positioning the body in proximity to an internal organ to be repositioned;
manipulating the body so that the tissue grasping element grasps a desired portion of tissue; and
applying tension to the at least one suspending member to reposition and secure the body organ.

60. The method of claim 59, wherein the medical instrument includes a mating element effective to enable the instrument to selectively mate with a positioning tool to facilitate positioning of the body.

61. The method of claim 59, wherein an actuating member is formed within the body and is effective to move the tissue grasping element selectively between the open and closed positions.

* * * * *